United States Patent [19]
Wei et al.

[11] Patent Number: 5,869,450
[45] Date of Patent: Feb. 9, 1999

[54] ANTI-INFLAMMATORY COMPOSITIONS AND METHOD WITH CORTICOTROPIN-RELEASING FACTOR ANALOGS

[75] Inventors: Edward T. Wei, Berkeley; Holly A. Thomas, Oakland, both of Calif.; Toshimitsu Kishimoto, Kobe, Japan

[73] Assignee: The Regents of the University of California, Oakland, Calif.

[21] Appl. No.: 611,537

[22] Filed: Mar. 6, 1996

[51] Int. Cl.$^6$ .......................... A61K 38/00; C07K 14/00
[52] U.S. Cl. .......................... 514/12; 530/306; 530/324
[58] Field of Search ........................ 530/324, 306; 514/12

[56] References Cited

U.S. PATENT DOCUMENTS

| | | | |
|---|---|---|---|
| 4,801,612 | 1/1989 | Wei et al. | 514/12 |
| 5,112,809 | 5/1992 | Rivier et al. | 514/12 |
| 5,137,871 | 8/1992 | Wei | 514/12 |
| 5,177,060 | 1/1993 | Wei | 514/15 |
| 5,306,710 | 4/1994 | Wei | 514/12 |
| 5,374,621 | 12/1994 | Wei | 514/14 |
| 5,480,869 | 1/1996 | Wei et al. | 514/16 |
| 5,488,033 | 1/1996 | Wei | 514/12 |

OTHER PUBLICATIONS

Chen et al., "Corticotropin Releasing Factor Receptor–Mediated Stimulation of Adenylate Cyclase Activity in the Rat Brain," *Brain Research,* 381:1, pp. 49–57 (Aug. 1986).

Sutton et al., Endocrinology 136 No. 3 pp. 1097–1101 (Mar. 1995).

Behan et al., "Displacement of Corticotropin Releasing Factor from its Binding Protein as a Possible Treatment for Alzheimer's Disease," *Nature,* 378, pp. 284–286 (1995).

Kishimoto et al., "A Sauvagine/Corticotropin–Releasing Factor Receptor Expressed in Heart and Skeletal Muscle," *Proc. Natl. Acad. Sci. USA,* 92, pp. 1108–1112 (1995).

Kornreich et al., "Alanine Series of Ovine Corticotropin Releasing Factor (oCRF): A Structure–Activity Relationship Study," *J. Med. Chem.,* 35, pp. 1870–1876 (1992).

Lightman, Stafford L., "From Stress to Cognition," *Nature,* 378, pp. 233–234 (1995).

Rivier et al., "Single Point D–Substituted Corticotropin–Releasing Factor Analogues: Effects on Potency and Physicochemical characteristics," *J. Med. Chem.,* 6, pp. 2851–2859 (1993).

Sutton et al., "Ligand Requirements of the Human Corticotropin–Releasing Factor–Binding Protein," *Endocrinology,* 136:3, pp. 1097–1102 (1995).

Vaughan et al., "Urocortin, a Mammalian Neuropeptide Related to Fish Urotensin I and to Corticotropin–Releasing Factor," *Nature,* 378, pp. 287–292 (1995).

Wei and Kiang, "Peptides of the Corticoliberin Superfamily Attenuate Thermal and Neurogenic Inflammation in Rat Pawskin," *Eur. J. Pharmacol.,* 68, pp. 81–86 (1989).

Wei and Thomas, "Correlation of Neuroendocrine and Anti–Edema Activities of Alanine–Corticotropin–Releasing Factor Analogs," *Eur. J. Pharmacol.,* 263, pp. 319–321 (1994).

*Primary Examiner*—Cecilia J. Tsang
*Assistant Examiner*—Bennett Celsa
*Attorney, Agent, or Firm*—Majestic, Parsons, Siebert & Hsue

[57] ABSTRACT

Peptide analogues are provided with amino acid sequences of the corticotropin-releasing factor superfamily, but having at least one amino acid residue that has been replaced with a D-amino acid residue or a D-amino acid analog. The peptide analogues have anti-inflammatory activity while having a receptor selectivity and thus a disassociated ACTH response.

8 Claims, 3 Drawing Sheets

ANTI-INFLAMMATORY COMPOSITIONS AND METHOD WITH CORTICOTROPIN-RELEASING FACTOR ANALOGS

GOVERNMENT INTEREST

This invention was made with government support under Grant No. DA-00091, awarded by the National Institutes of Health. The government has certain rights in this invention.

FIELD OF THE INVENTION

The invention generally relates to a method of inhibiting inflammation and more particularly to the use of certain novel corticotropin-releasing factor ("CRF") analogs having anti-edema activity, which activity is substantially independent of,, or disassociated from, adrenocorticotropin ("ACTH") release.

BACKGROUND OF THE INVENTION

The vascular tree is a complex network of blood vessels designed to maintain, at its outermost subdivisions, a surface area between blood and tissues for the exchange of gases and nutrients and for the drainage of waste products. During the early stages of inflammation, the sensitive mechanisms relating to microvascular perfusion are altered so that vascular integrity is compromised, blood contents leak into tissues, and hemostasis may develop. In the whole organism, severe and abrupt injury to the microcirculation distorts tissue architecture, impedes delivery of oxygen to cells, and causes extensive fluid loss from the vascular compartment, leading to edema, electrolyte imbalance, shock, and other circulatory disorders. The search for and identification of agents that modulate the immediate responses of inflammation may generate drugs with clinical benefit.

Studies have shown that certain peptides can act as agonists to inhibit inflammation, defined by Cotran et al. (*Robbins: Pathologic Basis of Disease,* (4th ed., 1989), Ed. Robbins, 2:39–86, Philadelphia: Saunders) as the reaction of vascularized living tissue to local injury. Specific antagonists, by design, work one-on-one against substances that promote inflammation, and the efficacy of a single antagonist may be limited if more than one mediator is released during tissue injury. An agonist, a term introduced by Reuse (*Br. J. Pharmacol.,* 3, pp. 129–62 (1948)) to describe a chemical that activates biological events, would be more efficacious than an antagonist if it could suppress convergent processes initiated by more than one inflammatory mediator. The concept of drugs as anti-inflammatory agonists was discussed by Svensjo and Persson in 1985 (*Handbook of Inflammation,* Ed. Bonta, 5:51–82, Amsterdam: Elsevier) and by Wei and Thomas ("Anti-Inflammatory Peptide Agonists," *Annual Review of Pharmacology and Toxicology,* 33, pp. 91–108, 1993).

One or two of us have previously described several different types of peptides useful for anti-inflammatory methods. Thus, U.S. Pat. No. 4,682,930 issued Jan. 9, 1996, titled "Anti-Inflammatory Composition and Method with Des-Tyr Dynorphin and Analogues," inventors Wei and Thomas, describe compounds of the dynorphin family as anti-inflammatory agents.

U.S. Pat. No. 5,480,869, issued Jan. 2, 1996, titled "Anti-Inflammatory Peptide Analogues and Treatment to Inhibit Vascular Leakage in Injured Tissues," inventors Wei and Thomas, describe small peptides having a six amino acid core where one of the amino acid moieties is in the D-configuration.

U.S. Pat. No. 5,374,621, issued Dec. 20, 1994, titled "Neurotensin and Method for Inhibiting Vascular Leakage," inventor Wei, describes neurotensin and analogs useful for anti-inflammatory purposes. Neurotensin is a 13-amino acid residue peptide and is related to an 8-residue peptide, named xenopsin. These peptides affect various physiological functions, such as blood flow, digestion and temperature regulation.

Corticotropin-releasing factor (CRF, also called CRH or corticoliberin) was first characterized as a 41-residue peptide isolated from ovine hypothalami by Vale et al. (1981). Subsequently, the sequence of human-CRF was deduced from cDNA studies and shown to be identical to rat-CRF, and then caprine, bovine, porcine, and white sucker fish CRF were characterized. The CRF of hoofed animals show considerable differences from man, but the pig and fish sequences differ from the human/rat sequence by only 2 out of 41 residues.

Peptides with homologous structures to mammalian CRF are found in cells of certain frog skins and in the urophysis of fish. In fact, the structure of sauvagine, the 40 amino acid peptide isolated from the skins of Phyllomedusa frogs, was reported several years before Vale's description of ovine-CRF in 1981. The structure of sucker fish urotensin I was reported just months after the description of ovine-CRF and resulted from an independent line of inquiry by Lederis's group in Canada. Although sauvagine and urotensin I release adrenocorticotropin (ACTH) from the pituitary, the natural physiological functions of these peptides in the tree-frog (Phyllomedusa species that live in arid regions of South America) and in the sucker fish remain unknown. The mystery deepened when Lederis' group (Okawara et al., "Cloning and Sequence Analysis of cDNA for Corticotropin-Releasing Factor Precursor from the Teleost Fish *Catostomus commersoni,* " *Proc. Natl. Acad. Sci.,* 85:22, pp. 8439–43 (1988)) showed that the sucker fish not only had urotensin I in its tail-organ but also had CRF in its brain. The co-existence of CRF and urotensin I in the sucker fish suggested that there were other CRF-like peptides in mammals. Vaughan et al., "Urocortin, a Mammalian Neuropeptide Related to Fish Urotensin I and to Corticotropin-Releasing Factor," *Nature,* 378:6554, pp. 287–92 (Nov. 1995), using antibodies to urotensin I as an investigative tool, recently discovered a CRF-like peptide in rat brain which was called urocortin. The functional interrelationships and amino acid sequences of CRF superfamily peptides which include CRF, urotensin I-like peptides, and sauvagine are known to the art.

Receptor proteins for CRF were first cloned in 1993 and shown to belong to the second family of 7-transmembrane domain $G_s$-protein coupled receptors. Two different genes were described encoding the receptors, CRF-R1 and CRF-R2, there being two different splice variants, α and β, for CRF-R2. The distribution of messenger RNA (mRNA) that codes for the synthesis of CRF-R1 is predominantly located in the pituitary, cerebellum, cerebral cortex and olfactory bulb and corresponds well with the location of immunoreactive CRF materials in the brain, as well as CRF binding sites as measured by radio-iodinated ligands. These results indicated that CRF-R1 was the receptor for endogenous CRF and moreover, this relationship was coupled to ACTH release. CRF-R2, however, was found to have a distribution that had little correspondence to the known sites of CRF synthesis. For example, CRF-R2 is found the heart muscle, lung and arterioles of peripheral tissues, but mRNA for CRF synthesis is not found in such tissues.

The pharmacological profile (or pattern of responsiveness) of CRF-R2 receptors to activation by peptides of the CRF superfamily was also clearly different from CRF-R1. Cells transfected with CRF-R1 and CRF-R2 are both sensitive to the cAMP stimulatory effects of human/rat CRF, frog sauvagine, sucker fish urotensin I and rat urocortin. However, the rank order of potency for cAMP stimulation in cells expressing the CRF-R2 receptor was sauvagine>urotensin I=urocortin >h/rCRF whereas sauvagine, urotensin I, urocortin and h/rCRF were about equipotent in cells transfected with CRF-R1 receptor. In assays for ACTH-release, sauvagine and urotensin I are about equipotent to h/rCRF, so again, based on pharmacological profile, it is clear that CRF-R1 is coupled to ACTH-release in physiological systems. The functional activities coupled to CRF-R2 activation are less clear, although it would appear that the natural hormone for activating this system is an urocortin or an urotensin I-like peptide, instead of a CRF-like peptide. In an earlier study (Wei and Kiang, "Peptides of the Corticoliberin Superfamily Inhibit Thermal and Neurogenic Inflammation," *European Journal of Pharmacology*, 168, pp. 81–86, 1989), it was shown that the intravenous potencies (measured as the median effective dose or ED50) of sauvagine, urotensin I and h/r CRF for suppression of heat-induced edema in the rat were 0.44, 1.5, and 5.9 nmol/kg, respectively. This pharmacological profile, when linked with the fact that CRF-R2 are located in peripheral tissues, indicated that selective activity of agonists at the CRF-R2 receptor paralleled anti-edema potency.

In summary, CRF regulates ACTH secretion via CRF-R1 receptors located on the anterior pituitary. CRF also has several direct actions on central and peripheral tissues, for example CRF has anti-inflammatory inflammatory properties and may have beneficial effects in Alzheimer's disease because it enhances learning and memory in animal models. In these actions on inflammation and memory, CRF is acting mainly on CRF-R2. The natural ligand for CRF-R2 may be peptides such as urocortin, which resemble more closely urotensin I, the peptide that was first identified in fish.

Some therapeutic methods and uses for CRF are described by U.S. Pat. No. 4,801,612, inventors Wei and Kiang, issued Jan. 31, 1989, titled "Method of Inhibiting Inflammatory Response," and U.S. Pat. No. 5,306,710, issued Apr. 26, 1994, titled "Method for Treating Endotoxin Shock with CRF," inventor Wei, which describes use of a CRF to decrease the leakage of blood components into brain tissue produced by various adverse medical conditions, and thus to treat a patient for injury to or disease of the brain, central nervous system or musculature in which edema is a factor.

However, the anti-edema activity of CRF is also associated with its ACTH-releasing activity. This is disadvantageous therapeutically because excessive steroid release can lead to adverse effects, a constellation of symptoms and signs called "Cushing's Syndrome," exhibiting effects such as a loss of muscle mass, thinning of bone, redistribution of fat, etc. Accordingly, a compound for therapeutic use with a more selective anti-edema property but having a reduced, or disassociated, ACTH release would be therapeutically beneficial.

Another limiting factor in the actions of CRF is its binding to CRF binding protein. This protein present in the body, especially in the brain, complexes to CRF with high affinity and reduces the available amount of "free" CRF for pharmacological actions. One approach to reduce CRF's ability to bind to the binding protein has been to modify the human/rat CRF to more closely resemble the ovine variant of CRF. A group of researchers has described some ligand requirements for CRF binding protein in *Endocrinology*, 136:3, pp. 1097–1102 (Sutton et al., 1995). They showed that in the regions where human/rat CRF differ from ovine CRF, namely, residues 22, 23, and 24 in the 41-amino acid peptide, conversion of the human residues, Ala, Arg and Glu to Thr, Lys, and Asp removes affinity of the variant for the binding protein. Thus, in the synthesis of new analogs, the changes in these three residues will increase the amount of "free" CRSF for pharmacological activities.

Another approach taken in attempts to modify the CRF peptide has been to shorten its overall length. Thus, elimination of resides 1–4 at the N-terminus of ovine CRF has been shown to not alter biological activities or ACTH-release potency. (See Kornreich, *J. Med. Chem.*, 35, pp. 1870–1876 (1992).) Although chemical manipulation of the CRF molecule has modest success in modifying the affinity of CRF for binding protein, and a modest shortening of its length whilst retaining activity, as well as increasing its potency for ACTH-release, so far the features of the CRF that determine receptor selectivity have not been identified. However, a CRF-like compound would be therapeutically useful if it had an anti-edema property but also had reduced, or disassociated, ACTH release.

SUMMARY OF THE INVENTION

It is the object of the present invention to provide CRF analogs useful as anti-inflammatory agents while having a receptor selectivity and thus a disassociated ACTH response for their anti-inflammatory property.

Peptide analogs are provided with amino acid sequences of the CRF superfamily but wherein at least one amino acid residue has been replaced with a D-amino acid residue or analog thereof, where peptides having 40 amino acid residues have the fourth such residue from the N-terminus modified by inclusion of a D-amino acid residue or analog whereas peptides having 41 amino acid residues have the fifth such residue from the N-terminus replaced with a D-amino acid residue or analog. Peptides of the invention are also preferably further modified in one or more of positions 22, 23, and 25 (from the N-terminus and with respect to 41 amino acid containing peptides). These additional modifications are chosen to reduce binding to the CRF binding protein; nevertheless, the inventive peptide analogs continue to have anti-inflammatory activity.

Thus, an important aspect for the invention is to provide selective CRF receptor agonists. CRF itself acts on both CRF-R1 and CRF-R2. But we believe that, by modifying the structure of CRF and related peptides, sauvagine, and urocortin, we are able to achieve selectivity for one of the receptor subtypes, namely CRF-R2. Selectivity is desirable because one can then have "purer" pharmacological effects, e.g. anti-inflammatory action, without concomitant ACTH-release.

Detailed Description of the Preferred Embodiments

The present invention provides novel CRF compounds that are analogs of the CRF superfamily of peptides. By "CRF superfamily" is meant to include those peptides recognized by the art as belonging to the CRF family due to many sequence similarities and similar biological activities.

Thus, the CRF superfamily includes the CRF peptides originating with or derived from a number of species, e.g., rat, human, pig, sheep ("ovine"), cow, and fish, and also includes sauvagine, urotensin I, and most recently urocortin. Urocortin is a mammalian neuropeptide recently described by Vaughan et al., *Nature*, 378, pp. 287–292 (1995). The amino acid sequences of these peptides are well known.

The novel CRF peptides of this invention are based upon our discovery that replacing the fifth amino acid (in the case of those 41 amino acid residue containing peptides of this family) or the fourth amino acid (for 40 amino acids residue containing peptides of the family) with a D-amino acid or a D-amino acid analog reduces ACTH-releasing activity while preserving anti-inflammatory activity. Other modifications and aspects of novel peptides for this invention will be further described after the following description reviewing uses to which the novel peptides may be put.

The neuropeptides should be administered under the guidance of a physician. Administration is preferably by intravenous, intradermal, or subcutaneous injection or delivered by oral or nasal inhalation. Administration can be within about two weeks before or after injury, preferably about two hours before deliberate lacerations of the musculature, brain surgery, or the like, and preferably up to about three days after surgery or accidental injury. The drug is preferably delivered via the bloodstream, but local injections into the cerebrospinal fluid, brain, or into the muscle can be used for administration.

Therapeutically effective doses of the inventive CRF analogs in practicing this invention are at least about 0.01 $\mu$g/kg, more preferably from about 0.1 to about 200 $\mu$g/kg, and most preferably are from about 0.1 to about 50 $\mu$g/kg. A particularly preferred dose is about 1 to about 30 $\mu$g/kg administered i.v. or subcutaneously. The dose may be infused slowly intradermally or subcutaneously, or may be injected directly into an afflicted body part, or delivered by nasal or oral inhalation. When injected locally, doses of about 10 to about 100 $\mu$g per local administration (i.e. about 0.1 to about 1 $\mu$g/kg body weight) are preferred.

Because novel peptides of this invention have the property of inhibiting vascular leakage from tissues, they are useful in a number of different therapeutic, anti-inflammatory applications. Specific tissues for which clinical usage of these peptides may be applied include skin and mucosal membranes (eyelids, nasal membranes, oropharyngeal membranes, upper respiratory tract, esophagus, lower digestive tract), skeletal muscle, smooth muscle, cardiac muscle, blood vessels of the brain, and blood vessels of the lungs and kidneys.

For example, therapeutic uses of these novel peptides include administration to treat thermal burns, irradiation burns, frostbite, or for other inflammatory conditions of the skin. The peptides may be used to reduce swelling, pain, and plasma extravasation. For irritants deposited on the upper airways or in chronic allergic conditions such as asthma, the peptides may be used to decrease irritancy, bronchial inflammation, edema and plasma extravasation. For lacerative or traumatic injuries to all tissues, such as might occur after knife wounds, surgical operations, and automobile accidents, the peptides may be used to reduce swelling, pain, and inflammation. For tissue infarcts, which result in tissue hypoxia, ischemic anoxia and edema, such as occur after brain strokes or myocardial infarcts, the peptides may be used to reduce passage of blood constituents into the tissue matrix and enhance survival of the remaining tissues. For preventing the actions of endogenous or exogenous chemicals that directly injure the endothelium, such as endotoxins or inflammatory mediators, resulting in the clinical condition of septic shock, the peptides may be useful in reducing the loss of blood volume and relaxing vascular smooth muscles. For attenuating inflammatory processes that attend autoimmune diseases such as rheumatoid arthritis and osteoarthritis, the peptides may be useful in reducing pain and swelling.

Yet further, administration may be used for preserving the integrity of the vascular tree of an organ prior to or during its removal for transplantation, such organs being for example kidneys, lungs, liver, or heart.

The active neuropeptides of this invention may be administered in combination with a pharmaceutically acceptable carrier, such as isotonic saline, phosphate buffer solution, or the like. Topical administration is not as preferred as injection, since the CRF analogs are large molecules (e.g., 40 or 41 amino acids) and are not as efficiently delivered to the site of action as when administered by injection. Oral and nasal administrations strations are possible. Excipients and adjuvants useful in formulating such compositions are well known.

Although the peptides are generally water soluble as typically synthesized, they may be administered in the form of pharmaceutically acceptable non-toxic salts, such as acid addition salts. Illustrative acid addition salts are hydrochloride, hydrobromide, sulfate, sulphate, acetate, citrate, benzoate, succinate, malate, ascorbate, tartrate, or the like.

Figure 1:
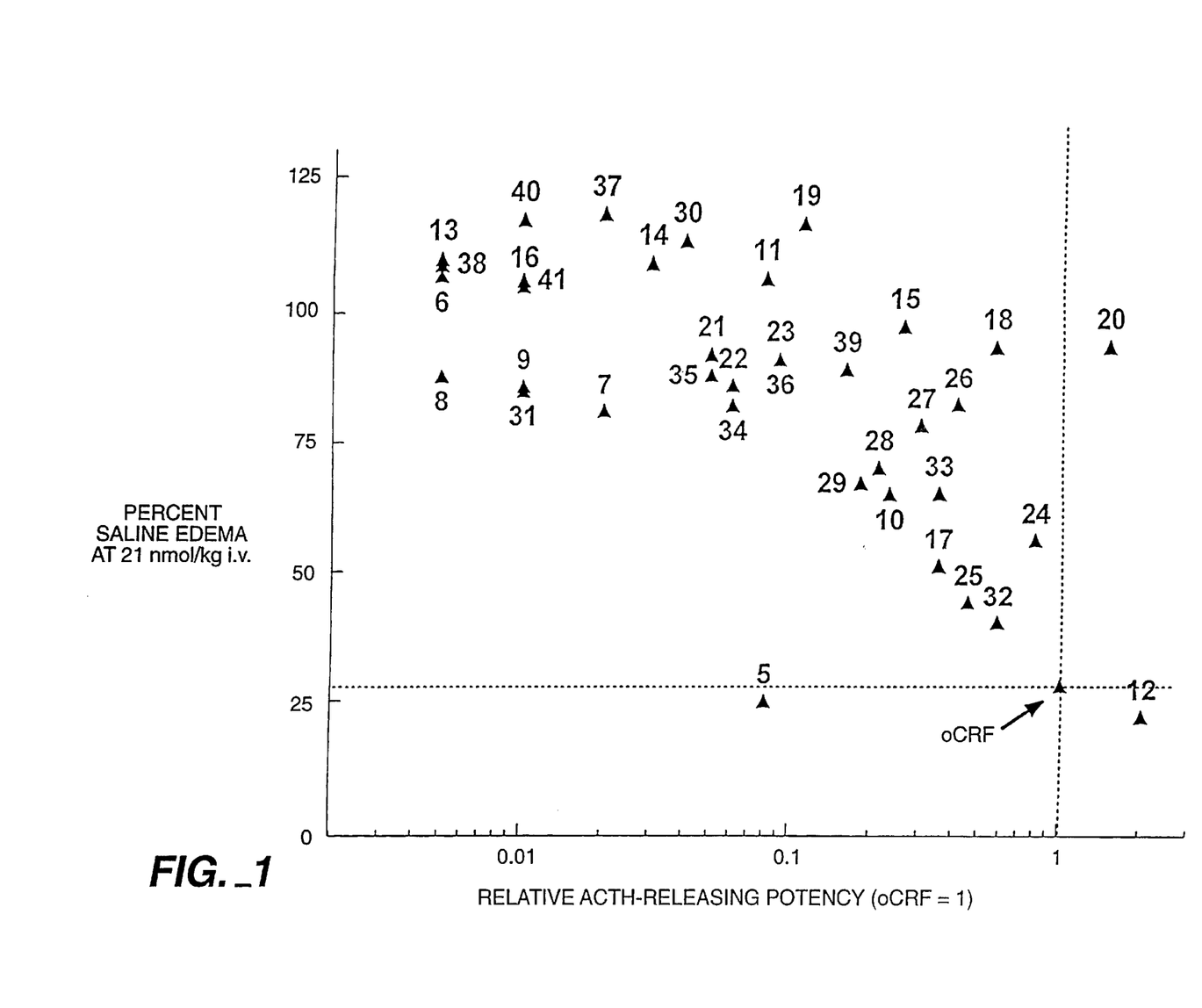
FIG. 1 graphically illustrates relative ACTH-releasing potency plotted against anti-edema activity for 37 different ovine CRF analogues, one of which (5) is a preferred embodiment of the subject invention.

Turning to FIG. 1, 37 different ovine CRF analogs were singly substituted with a D-amino acid and screened for suppression of heat-induced edema and relative ACTH-releasing potency. As can be seen, substitution of the fifth position proline with D-Pro left a peptide that was relatively low in ACTH-releasing potency, but still gave anti-edema activity. The ovine corresponding analog has the sequence:

SQEPpISLDL TFHLLREVLE MTKADQLAQQ AHSNRKLLDIA (wherein "p" stands for the D-amino acid or analog). Indeed, this [D-Pro$^5$] CRF analog is at least equipotent to unmodified oCRF in anti-inflammatory activity, but it retains only 8% of the ACTH-releasing potency relative the unmodified peptide.

The data shown by FIG. 1 as to the novel [D-Pro$^5$] CRF analog was a surprising result because in screenings of 33 other (differently modified) CRF-related peptides reported in 1994, Wei and Thomas, *Eur. J. Pharmacol.*, 263, pp. 319–321, was found a strong positive rank correlation between the anti-edema and neuroendocrine activities.

In a manner similar to the novel ovine derived [D-Pro$^5$] CRF analog, the human/rat derived [D-Pro$^5$] CRF analog was synthesized and was found to be equipotent to human/rat CRF for suppression of heat-edema.

The claimed CRF analogs may be synthesized using the desired amino acids and amino acid analogs, the active groups of which may be protected as required using, for example, a t-butyldicarbonate (t-BOC) group or a fluorenylmethoxy carbonyl (FMOC) group. Suitable amino acids and amino acid analogs can be purchased commercially (Sigma Chemical Co.; Advanced Chemtec) or synthesized using methods known in the art. Peptides synthesized using the solid phase method can be attached to resins including 4-methylbenzhydrylamine (MBHA), 4-(oxymethyl)-phenylacetamido methyl and 4-(hydroxymethyl)-phenoxymethyl-copoly(styrene-1% divinylbenezene; Wang resin), all of which are commercially available, or to p-nitrobenzophenone oxime polymer (oxime resin), which can be synthesized as known to the art.

Thus, peptide analogs of this invention correspond substantially to the amino acid sequences of the CRF superfamily, but wherein at least one amino acid residue has been replaced with a D-amino acid residue or analog. Peptides having 40 amino acid residues have the fourth such residue from the N-terminus modified by inclusion of a D-amino acid residue or analog whereas peptides having 41 amino acid residues have the fifth such residue from the N-terminus replaced with a D-amino acid residue or analog. Among the suitable D-amino acids are proline.

The chemical name of proline is 2-pyrrolidine carboxylic acid. In the standard drawing of this secondary amino acid, the carboxylic acid function is protruding from the paper in the L-configuration and pointed into the paper in the D-configuration. In the CRF superfamily peptides, the residue preceding $Pro^4$ or $Pro^5$ is invariably another proline. Proline itself, because of the unusual rigidity in structure conferred by the secondary amino group on the α-carbon, imposes conformational restraint on the rotation and flexibility of the amino acid residues within its molecular vicinity. Thus, the orientation of L-Pro-L-Pro compared to L-Pro-D-Pro (or more generally L-Pro-"D-amino acid or analog") is significantly different and creates the selectivity for the two types of CRF receptors.

It should be noted, however, that there are a number of alternative possibilities for replacing D-Pro with other similar entities or amino acid substituents and these alternatives are known to those skilled in the art of peptide synthesis. We generally mean to describe these alternative possibilities as being a "D-amino acid analog." By this is meant to include moieties having a molecular weight of less than about 1000 daltons. More typically the selected D-amino acid analogs will be relatively small, such as preferably on the order of about 100 daltons to about 200 daltons, and with an asymmetrical α-carbon (as a chiral center) in the D-configuration. A variety of suitable alternatives to the usual D-amino acids are available from commercial sources. Illustrative compounds for the D-amino acids and analogs are those derived from the Formula 1 structures:

FORMULA 1 where $R_1$ is H, $CH_3$, $CH_2$-Ph, $CH_2$-pyridyl, $CH_2$-imidazole, $CH_2$-indole, $CH_2$—$(CH_2)_2COOH$, $CH_2$—$(CH_2)_2CONHR_3$, $CH_2$—$(CH_2)_nNHR_3$, $CH_2$—$(CH_2)_nSR_3$, $CH_2$—$(CH_2)_nNC(NH)NH_2$, or $CH_2$—$(CH_2)_nOH$; $R_2$ is OH, $NH_2$, SH, $NHCH_3$, $N(CH_3)_2$, $NHCH_2Ph$, or $OR_3$; $R_3$ is H, $CH_3$, or a linear or branched alkyl having 2 to 6 carbons; n is 0, 1, 2, or 3; and "*" denotes the chiral center at the α-carbon.

For example, D-Pro can be replaced with 4-hydroxy-D-Pro, D-thioproline, and 5-oxo-D-Pro, or by heterocyclic alternatives such as D-Tic (D-1,2,3,4-tetrahydroisoquinolinic-3-carboxylic acid), D-Oic (octahydro-indolyl-2-carboxylic acid), and D-Isonipecotic acid (4-piperidine carboxylic acid) derivatives.

The residues which are isosteric and/or homologous to D-Pro can confer an equivalent or better degree of receptor selectivity. The key structural element discovered in this invention is the importance and significance of a D-configuration of the α-carbon moiety, be it from a D-amino acid or D-amino acid analog, in the fourth or fifth residue of the CRF superfamily peptide that confers receptor selectivity.

Peptides of the invention are also preferably further modified in one or more of positions 22, 23, and 25 (from the N-terminus and with respect to 41 amino acid containing peptides). These additional modifications are chosen to reduce binding to the CRF binding protein; nevertheless, the inventive peptide analogs continue to have anti-inflammatory activity, as can be readily ascertained by a screening assay, such as the screening assay described by Example 1.

As earlier discussed, an aspect for this invention is to provide selective CRF antagonists.

Selectivity for one of the receptors subtypes, namely CRF-R2, is desirable because one can obtain a desired pharmaceutical effect, such as anti-inflammatory action, without concomitant ACTH-release.

Selective agonists in other fields of receptor interaction are known. For example, in treating asthma β2-adrenergic drugs relax bronchial smooth muscle. β-Adrenergic receptors exist in many parts of the body. Stimulation of these receptors in the heart increases the rate and force of heart muscle contraction (β1-adrenergic receptors). Stimulation of other β2-adrenergic receptors in the bronchial smooth muscles relaxes the muscle and results in increased airway diameter, permitting greater ease of breathing (a desirable result in asthma).

Epinephrine, an endogenous hormone, is an example of a chemical substance that is a relatively non-selective β-adrenergic receptor agonist (defined as a chemical that activates biological systems): it will act on both the heart muscle and the bronchial smooth muscle. Cardiac acceleration is not desirable because it may lead to arrhythmias. Examples of selective β2-adrenergic drugs are albuterol and terbutaline: these drugs, which are structural modifications of the epinephrine molecule, preferentially stimulate the receptors in the bronchial smooth muscle (β2-adrenergic receptor agonists) and have less actions on the heart. They are preferred to epinephrine in the treatment of asthma.

Thus, the present invention provides a new class of selective receptor agonists, particularly having CRF-R2 selectivity.

Aspects of the invention will now be exemplified by the following examples, which are intended to illustrate but not to limit the invention.

EXAMPLE 1

This example illustrates the anti-inflammatory property of inventive peptide embodiments by comparison with human/rat CRF as a control, and may be readily used by analogy in screening for other embodiments of the invention.

The index of anti-inflammatory activity was measured as suppression by heat-induced edema. Briefly, male Sprague-Dawley rats weighing 200–250 g were anesthetized with sodium pentobarbital (60 mg/kg i.p.). Saline (1 ml/kg body weight) or test substances dissolved in saline were injected i.v. via a branch of the femoral vein. Ten minutes after injection, thermal stimulus was applied to the hind paw by immersion of the foot, up to the ankle joint, in 58° C. water for 1 minute. Thirty minutes after heat exposure, animals were killed by overdose with concentrated sodium pentobarbital and both hind paws were removed at the ankle joint and weighed. The degree of heat-induced edema was estimated as the difference between the weights of the heated and unheated paws divided by the weight of the unheated paw. Four to six analogs (N≧3 animals per dose level with 3 to 4 dose levels per analog) were tested on each occasion with concurrent saline controls. The median effective dose ($ED_{50}$) was calculated according to the method of Litchfield and Wilcoxon (1949).

Table 1, below, sets out the median effective dose for the control, for the [D-Pro$^5$] CRF analog already discussed, and also for another four different peptide embodiments of the invention.

TABLE 1A

| Peptide | ED$_{50}$ (95% CL) μg/kg i.v. |
|---|---|
| oCRF | 37 (18–79) |
| h/rCRF | 10 (3–28) |
| urocortin (rat) | 7 (2–21) |
| [D-Pro$^5$]oCRF | 19 (5–26) |
| Inventive Embodiments | |
| [D-Pro$^5$]CRFa | 10 (3–33) |
| [D-Pro$^5$, Thr$^{22}$, Lys$^{23}$, Asp$^{25}$]CRFa | 19 (9–38) |
| [D-Pro$^4$]sauvagine | 6 (2–14) |
| [D-Pro$^5$]white sucker fish urotensin I | 9 (5–17) |
| [D-Pro$^4$]urocortin (rat) | 6 (2–16) | a human/rat

As shown by Table 1A, the novel peptide embodiment of the invention, [D-Pro$^5$] human/rat CRF, was prepared where the normal 5 position proline of CRF had been substituted with D-proline. This [D-Pro$^5$] human/rat CRF analog embodiment of the invention provided equivalent anti-inflammatory results to that of the unmodified CRF (human/rat) control. A similarly substituted, white sucker fish urotensin I also provided about equivalent anti-inflammatory properties to the CRF control. This [D-Pro$^5$] white sucker fish urotensin I peptide is another embodiment of the invention. Two other inventive embodiments (D-Pro$^4$ substituted sauvagine and D-Pro$^4$ substituted urocortin) gave potent, anti-inflammatory, results.

As also shown by Table 1A, another inventive embodiment was prepared having the fifth position substituted with D-Pro, and also having three further substitutions: The normal alanine residue at position 22, the normal arginine residue at position 23 and the normal glutamic acid position at 25 were all changed to threonine, lysine and aspartic acid, respectively. This novel peptide of the invention also gave an anti-inflammatory response.

The structures of the five novel peptide embodiments are shown in Table 1B.

Figure 2:
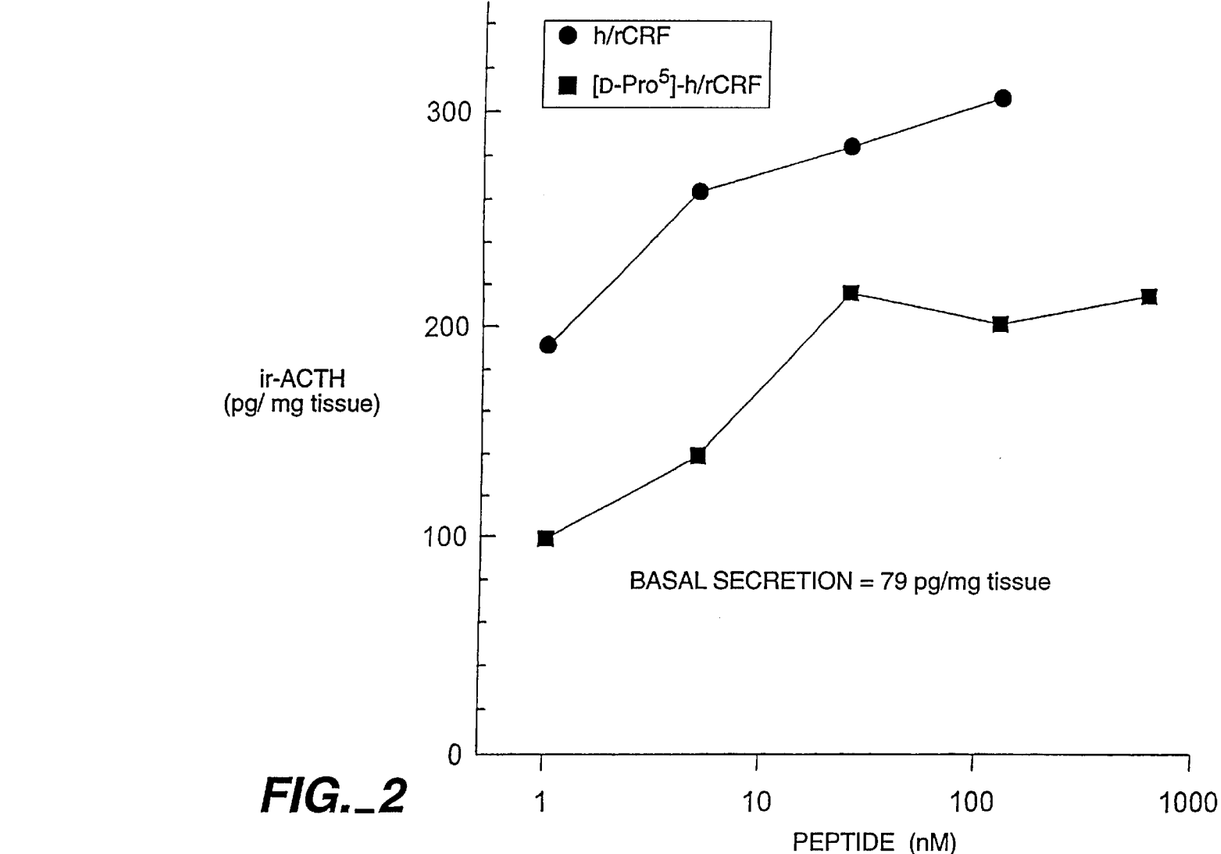
FIG. 2 graphically illustrates radio-immuno assay measurements of ACTH as a function of peptide concentration for the prior art peptide, human/rat CRF and for a preferred embodiment of the invention.

In determining ACTH release, an useful assay system to measure ACTH release by an in vitro assay is where basal or CRF-induced ACTH release is measured in the manner described by Vale et al. ("Assay of Corticotropin Releasing Factor," Methods in Enzymology: Neuroendocrine Peptides, 103, pp. 565–577, Conn. Ed., Academic Press, New York, 1983). The results shown in FIG. 2 were obtained by incubating the test peptides with segments of rat pituitary cells. After incubation the ACTH in the fluid bathing these segments were measured by radioimmunoassay (ir-ACTH) in units of pg of ACTH per mg of pituitary tissue. As can be seen in FIG. 2, the basal release of ACTH is 79 pg/mg tissue. After the addition of CRF, this is increased in a dose-dependent relationship. Modification of Pro$^5$ to D-Pro$^5$ in the CRF molecule decreases the potency of the peptide for ACTH release by at least 10-fold, which is consistent with the data obtained by Kornreich et al. for ovine-CRF. However, the anti-edema potencies between these two peptides were identical.

EXAMPLE 3

Figure 3A:
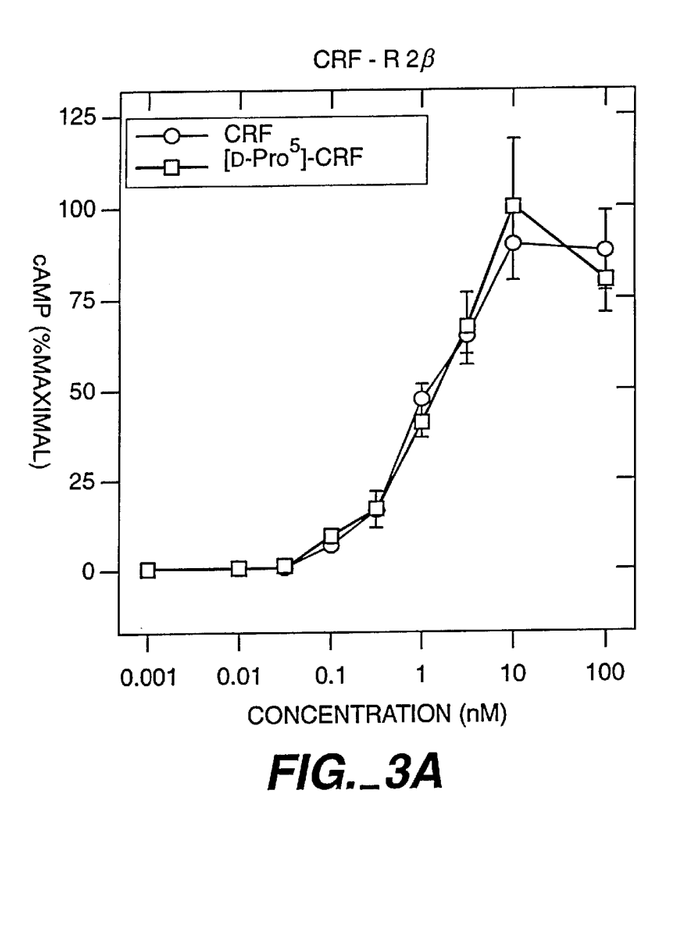
FIG. 3 graphically illustrates cells that were transfected with CRF receptors and sensitive to the CAMP stimulatory effects of CRF when tested with the prior art CRF itself or with a preferred embodiment of the invention.
Figure 3B:
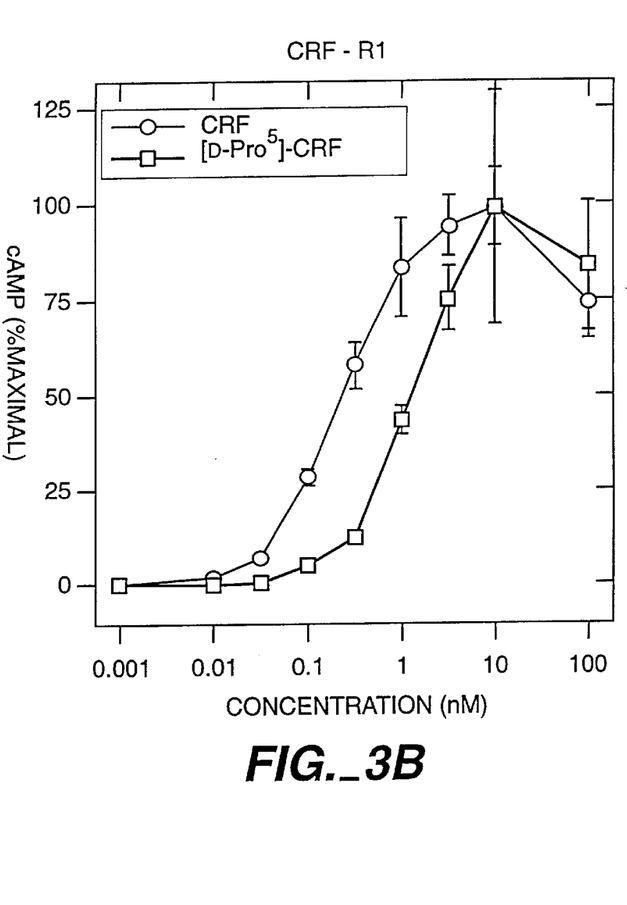

For another assay, two types of cloned CRF receptors were assessed for their responses to the CRF analogs. These were the pituitary-central nervous system (PC)-CRF receptor and the heart muscle (HM)-CRF receptor, also called CRF-R1 and CRF-R2β. Cells were transfected with the full-length cDNA of these receptors. These procedures were performed according to Chang et al., Neuron, 11, pp. 1187–1195 (1993) and Kishimoto et al., Proc. Natl. Acad. Sci. USA, 92, pp. 1108 (1995). cDNAS for the PC-CRF receptor and the HM-CRF receptor were subcloned into expression vector pCEP4 and transfected into 293-EBNA cells. Stable transfectants were incubated with 50 μM 3-isobutylmethyl-1-methylxanthine for 20 minutes at 37° C. and then peptides were added and incubated for another 20 minutes at 37° C. Levels of cAMP were assayed in sextuplicate. Cells transfected with these CRF receptors are sensitive to the cAMP stimulatory effects of CRF. The results for h/rCRF and [D-Pro$^5$]h/rCRF are shown in FIG. 3. It can be seen that the potency of the CRF molecule for CRF-R1 is significantly reduced by about six-fold after replacement of residue Pro$^5$ by the corresponding D-amino acid. This change, however, does not apply to the CRF-R2β which maintains equivalent sensitivity. As noted previously, the anti-inflammatory potency of these two analogs were also identical.

TABLE 1B

Structures of CRF superfamily peptides modified for selective actions on receptors:

| | | |
|---|---|---|
| [D-Pro$^6$]CRF | Human | SEEPpISLDL TFHLLREVLE MARAEQLAQQ AHSNRKLMEII |
| [D-Pro$^6$, Thr$^{22}$, Lys$^{23}$, Asp$^{25}$]CRF | Human | SEEPpISLDL TFHLLREVLE MTKADQLAQQ AHSNRKLMEII |
| [D-Pro$^4$]Urocortin | Rat | DDPpLSIDL TFHLLRTLLE LARTQSQRER AEQNRIIFDSV |
| [D-Pro$^6$]CRF | Fish | SEEPpISLDL TFHLLREVLE MARAEQLAQQAHSNRKMMEIF |
| [D-Pro$^4$]Sauvagine | Frog | >EGPpISIDL SLELLRKMIE IEKQEKEKQQ AANNRLLLDTI | underlined residues indicate point of modification, p = D-Pro
a) The carboxyl termini of these peptides were amidated.
b) Single letter abbreviations for amino acids: S, T, P, A, G; Ser, Thr, Pro, Ala, Gly; M, L. I, V; Met, Leu, Ile, Val; E, D, N, Q; Glu, Asp, Asn, Gln; R, K, H; Arg, Lys, His; F, Y, W; Phe, Try, Trp: >E; pyroglutamyl.

EXAMPLE 2

Example 1 illustrates an assay for the anti-inflammatory property of novel peptides for this invention. We have further tested embodiments for selectivity in order to show that the two biological actions, suppression of edema and ACTH-release, have been selectively separated.

CRF superfamily peptides with D-amino acid substitutions on position 4 or 5 were able to activate the CRF-R1land CRF-R2β receptors, as shown in Table 2. Selectivity were retained in the analogs and the relative increment in receptor selectivity varied from 2.5-fold to 5.9-fold. Thus, the results confirm the hypothesis that receptor selectivity is conferred by changing residue 4 or 5 to a D-configuration.

TABLE 2

| Peptide | EC50 nM CRF-R1 | EC50 nM CRF-R2β | ED50 ratio CRF-R2β/ CRF-R1 | Increment in Selectivity |
|---|---|---|---|---|
| h/rCRF | 1.3 | 0.22 | 0.17 | |
| [D-Pro⁶]h/rCRF | 1.3 | 1.3 | 1 | 5.9 |
| sauvagine | 0.1 | 0.2 | 2 | |
| [D-Pro⁴]sauvagine | 0.75 | 7.0 | 9.3 | 4.7 |
| white sucker fish urotensin I | 0.5 | 0.2 | 0.4 | |
| [D-Pro⁵]white sucker fish urotensin I | 0.4 | 0.4 | 1 | 2.5 |
| urocortin (rat) | 0.15 | 0.32 | 2 | |
| [D-Pro⁴]urocortin (rat) | 0.20 | 1.00 | 5 | 2.5 |

EXAMPLE 4

The ligand requirements for CRF to complex with CRF binding protein were described by Sutton et al., *Endocrinology*, 136:3, pp. 1097–1102, 1995. They showed that in one of the regions where human/rat CRF differ from ovine CRF, namely, residues 22, 23, and 24 in the 41-amino acid peptide, conversion of the human residues, Ala, Arg and Glu to Thr, Lys, and Asp removes affinity of the variant for the binding protein.

To determine if modification of [D-Pro⁵]h/rCRF to [D-Pro⁵, Thr²², Lys²³, Asp²⁵]h/rCRF affected anti-inflammatory activity and if binding characteristics were altered we synthesized and compared the two analogs. As can be seen in the data below, [D-Pro⁵, Thr²², Lys²³, Asp²⁵] h/rCRF retained anti-inflammatory activity and the abilities to activate CRF receptors. The binding of [D-Pro⁵, Thr²², Lys²³, Asp²⁵]h/rCRF to CRF binding protein was assessed by the following method. Both peptides were radio-iodinated with $I^{125}$, incubated with CRF-binding protein, placed on a Sephadex G100 column and the fractions collected. [D-Pro⁵]h/rCRF formed a complex with binding protein and co-eluted in the fraction where h/rCRF-binding protein was eluted (a fraction which has a molecular weight of about 42,000 Daltons. On the other hand, [D-Pro⁵, Thr²², Lys²³, Asp²⁵]h/rCRF did not form a complex with binding protein and eluted with the fraction that corresponded to its molecular weight, namely, 4677 Daltons. These results clearly established that modification of [D-Pro⁵]h/rCRF to [D-Pro⁵, Thr²², Lys²³, Asp²⁵]h/rCRF did not significantly affect the ability of the peptide to activate CRF receptors, but had the added advantage that the analog now no longer complexed with binding protein.

TABLE 3

| Peptide | ED₅₀ (95% CL) μg/kg i.v. | EC50 nM CRF-R1 | EC50 nM CRF-R2 |
|---|---|---|---|
| [D-Pro⁵]h/rCRF | 10 | 1.3 | 1.3 |
| [D-Pro⁵, Thr²², Lys²³, Asp²⁵]h/rCRF | 19 | 1.5 | 4.5 |

As is illustrated by the examples, embodiments of the invention are able to discriminate between CRF receptors linked to neuroendocrine actions versus CRF receptors linked to anti-inflammatory effects. Thus, in addition to the various therapeutic applications such as earlier described, the inventive analogs, either radio-iodinated or in their native form, can be used as research tools in assays, such as competitive ligands in binding assays to discriminate between neuroendocrine and anti-inflammatory selectivity.

It is to be understood that while the invention has been described above in conjunction with preferred specific embodiments, the description and examples are intended to illustrate and not limit the scope of the invention, which is defined by the scope of the appended claims.

It is claimed:

1. A peptide analog of a Corticotropin-Releasing Factor (CRF) having the amino acid sequence of (a) human CRF or rat CRF, but wherein the fifth amino acid from the N-terminus is D-Proline, (b) urocortin or sauvagine, but wherein the fourth amino acid from the N-terminus is D-Proline, or (c) white suckerfish urotensin I, but wherein the fifth amino acid from the N-terminus is D-Proline, and wherein the analog has an anti-inflammatory activity in vivo.

2. The peptide analog as in claim 1 being human or rat CRF with the fifth amino acid from the N-terminus being D-Proline, and further having the twenty-second amino acid residue substituted with threonine, the twenty-third amino acid residue being substituted with lysine, and the twenty-fifth amino acid residue being substituted with aspartic acid.

3. The peptide analog as in claim 1 having the amino acid sequence of urocortin or sauvagine, but wherein the fourth amino acid from the N-terminus is D-Proline.

4. The peptide analog as in claim 3 wherein the anti-inflammatory activity is substantially independent of ACTH release.

5. A method of treating a patient suffering from an inflammatory condition comprising:

administering to the patient a peptide analog of a Corticotropin-Releasing Factor (CRF) having the amino acid sequence of (a) human CRF or rat CRF, but wherein the fifth amino acid from the N-terminus is D-Proline, (b) urocortin or sauvagine, but wherein the fourth amino acid from the N-terminus is D-Proline, or (c) white suckerfish urotensin I, but wherein the fifth amino acid from the N-terminus is D-Proline, and wherein the analog has an anti-inflammatory activity in vivo, the analog being effective in providing an anti-inflammatory activity in vivo that is substantially independent of ACTH release.

6. The method as in claim 5 wherein the amount of peptide analog administered is from about 1 μg to about 200 μg per kg of patient body weight.

7. The method as in claim 5 wherein the peptide analog administered is D-Pro⁴ substituted sauvagine or D-Pro⁴ substituted urocortin in an amount of from about 0.1 μg to about 200 μg per kg of patient body weight.

8. The method as in claim 7 wherein the peptide analog is administered in an amount of from about 1 μg to about 200 μg per kg of patient body weight.

* * * * *

UNITED STATES PATENT AND TRADEMARK OFFICE
CERTIFICATE OF CORRECTION

PATENT NO. : 5,869,450
DATED : February 9, 1999
INVENTOR(S) : Edward T. Wei et al.

It is certified that error appears in the above-identified patent and that said Letters Patent is hereby corrected as shown below:

Column 3, line 62 :

Replace: "22, 23, and 24"

With: --22, 23, and 25--

Signed and Sealed this

Twenty-ninth Day of June, 1999

Attest:

Attesting Officer

Q. TODD DICKINSON

Acting Commissioner of Patents and Trademarks